United States Patent [19]

Yoshida et al.

[11] Patent Number: 4,510,154
[45] Date of Patent: Apr. 9, 1985

[54] THIAZOLIDINE COMPOUND AND FUNGICIDAL COMPOSITION CONTAINING IT

[75] Inventors: Kenji Yoshida; Makoto Nakazawa, both of Sagamihara; Toyohiko Shike, Yokohama; Masayuki Tomida, Sagamihara; Masataka Tsuda, Machida; Toru Teraoka, Tokyo, all of Japan

[73] Assignee: Mitsubishi Chemical Industries Ltd., Tokyo, Japan

[21] Appl. No.: 484,502

[22] Filed: Apr. 13, 1983

[30] Foreign Application Priority Data

Apr. 21, 1982 [JP] Japan .................................. 57-66720
Oct. 19, 1982 [JP] Japan .................................. 57-183346

[51] Int. Cl.³ .................... C07D 417/06; A01N 43/78
[52] U.S. Cl. .................... 514/365; 548/146; 548/200; 548/201
[58] Field of Search .................... 548/200, 201, 146; 424/270

[56] References Cited

U.S. PATENT DOCUMENTS 4,011,233 3/1977 Dubs .................................. 548/146
4,332,950 6/1982 Kelly .................................. 548/146

Primary Examiner—Robert Gerstl
Attorney, Agent, or Firm—Oblon, Fisher, Spivak, McClelland & Maier

[57] ABSTRACT

A thiazolidine compound represented by the following general formula I or its acid addition salt

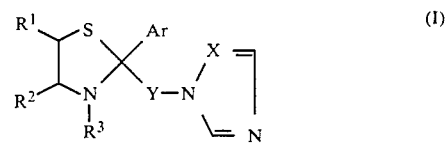

where X is —CH= or —N=, Y is

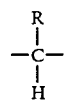

(where R is a hydrogen atom, a methyl group or an ethyl group) or —CH$_2$CH$_2$—, Ar is a phenyl group which may be substituted by halogen, lower alkyl, lower alkoxy, phenyl or trifluoromethyl, a thienyl group or a naphthyl group, R$^1$ is a hydrogen atom, a straight chain or branched chain alkyl group having from 1 to 10 carbon atoms or a phenyl group which may be substituted, R$^2$ is a hydrogen atom, a straight chain or branched chain alkyl group having from 1 to 10 carbon atoms, a phenyl group which may be substituted, a lower alkoxycarbonyl group, a lower alkylcarbamoyl group or a lower alkenylcarbamoyl group, and R$^3$ is a hydrogen atom, a lower alkyl group, a lower acyl group, a lower alkylcarbamoyl group, a lower alkylthiocarbamoyl group or a phenylcarbamoyl group. The compound is useful as fungicide.

12 Claims, No Drawings

THIAZOLIDINE COMPOUND AND FUNGICIDAL COMPOSITION CONTAINING IT

The present invention relates to thiazolidine compounds which are useful as a fungicide. More particularly, the present invention relates to a thiazolidine compound, a fungicidal composition containing it and a process for preparing the thiazolidine compound.

Certain imidazole derivatives or triazole derivatives are known to be effective as fungicides which are useful for the prevention of plant diseases. For instance, a commercially available fungicide known by the common name of benomyl is a compound having a benzimidazole ring, and a fungicide known by the common name of etaconazole is a compound having a triazole ring and a dioxolan ring. However, there has been no report on the physiological activities of a compound which has both an imidazole or triazole ring and a thiazolidine ring.

The present inventors have found that novel compounds having both the thiazolidine ring and the imidazole or triazole ring have strong fungicidal effectiveness against a wide range of plant diseases.

The present invention provides a thiazolidine compound represented by the following general formula I or its acid addition salt

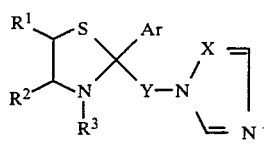

where X is —CH= or —N=, Y is

(where R is a hydrogen atom, a methyl group or an ethyl group) or —CH$_2$CH$_2$—, Ar is a phenyl group which may be substituted by halogen, lower alkyl, lower alkoxy, phenyl or trifluoromethyl, a thienyl group or a naphthyl group, R$^1$ is a hydrogen atom, a staight chain or branched chain alkyl group having from 1 to 10 carbon atoms or a phenyl group which may be substituted, R$^2$ is a hydrogen atom, a straight chain or branched chain alkyl group having from 1 to 10 carbon atoms, a phenyl group which may be substituted, a lower alkoxycarbonyl group, a lower alkylcarbamoyl group or a lower alkenylcarbamoyl group, and R$^3$ is a hydrogen atom, a lower alkyl group, a lower acyl group, a lower alkylcarbamoyl group, a lower alkylthiocarbamoyl group or a phenylcarbamoyl group.

Further, the present invention provides a fungicidal composition containing the thiazolidine compound of the general formula I or its acid addition salt as an active ingredient, and a process for preparing the thiazolidine compound.

Now, the present invention will be described in detail with reference to the preferred embodiments.

In the general formula I, Ar includes a phenyl group; a phenyl group substituted by halogen such as chlorine, bromine or fluorine, lower alkyl having from 1 to 4 carbon atoms such as methyl, ethyl, propyl or butyl, lower alkoxy having from 1 to 4 carbon atoms such as methoxy, ethoxy or propoxy, or- phenyl; a thienyl group; or a naphthyl group.

R$^1$ is a hydrogen atom; a straight chain or branched chain alkyl group having from 1 to 10 carbon atoms such as methyl, ethyl, propyl, butyl, pentyl, hexyl, heptyl, octyl, nonyl, decyl, isopropyl, isobutyl, sec-butyl, t-butyl, neopentyl or 2-ethylhexyl; or a phenyl group which may be substituted by lower alkyl or halogen. R$^2$ is a hydrogen atom; a straight chain or branched chain alkyl group having from 1 to 10, preferably from 1 to 6, carbon atoms such as methyl, ethyl, propyl, isobutyl, hexyl, heptyl, octyl, nonyl or decyl; a phenyl group which may be substituted by lower alkyl or halogen; a lower alkoxycarbonyl group such as methoxycarbonyl, ethoxycarbonyl, propoxycarbonyl or butoxycarbonyl; a carbamoyl group substituted by a lower alkyl group having from 1 to 4 carbon atoms such as methylcarbamoyl, propylcarbamoyl or butylcarbamoyl; or a carbamoyl group substituted by a lower alkenyl group having from 3 to 4 carbon atoms such as propenylamino carbonyl. R$^3$ is a hydrogen atom; a lower alkyl group having from 1 to 4 carbon atoms such as methyl, ethyl or propyl; a lower carboxyacyl group having from 2 to 5 carbon atoms such as acetyl or propionyl; a carbamoyl or thiocarbamoyl group substituted by a lower alkyl group having from 1 to 4 carbon atoms such as methylcarbamoyl, ethylcarbamoyl, propylcarbamoyl, butylcarbamoyl, methylthiocarbamoyl or propylthiocarbamoyl; or a phenylcarbamoyl group.

When the compound of the general formula I is in the form of an acid addition salt, the acid may be an inorganic acid or an organic acid such as hydrochloric acid, nitric acid, sulfuric acid, acetic acid, p-toluene sulfonic acid or oxalic acid.

From the standpoint of the fungicidal activity, Ar in the general formula is preferably a phenyl group substituted at its 2-position and/or 4-position by a halogen atom, X is preferably —N=, Y is preferably —CH$_2$—, and each of R$^1$, R$^2$ and R$^3$ is preferably a hydrogen atom or a lower alkyl group.

The thiazolidine compound represented by the general formula I may be prepared, for instance, by the following process.

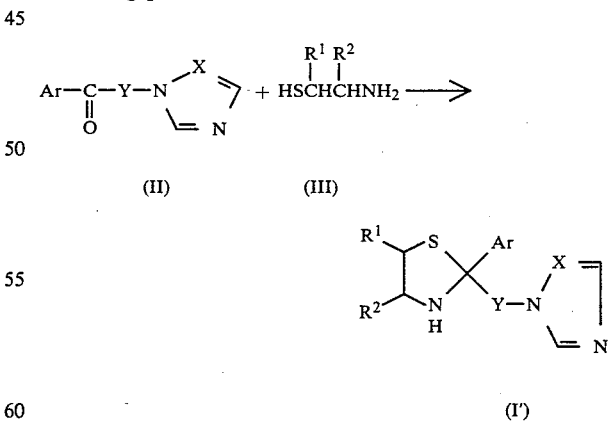

where X, Y, Ar, R$^1$ and R$^2$ are as defined above with respect to the above general formula I.

Namely, when an aryl ketone of the general formula II is reacted with a β-mercaptoethylamine of the general formula III, a compound of the general formula I', i.e. a compound of the general formula I where R$^3$ is a hydrogen atom, is obtained. A compound of the general formula I where $R^3$ is other than a hydrogen atom may be obtained, for instance, by reacting the compound of the formula I' with a lower alkyl halide, a lower acyl halide, a lower alkanoic acid anhydride, a lower alkylisocyanate, a lower alkylisothiocyanate or a phenylisocyanate.

The reaction of the aryl ketone of the formula II with the β-mercaptoethylamine of the formula III is carried out at a temperature of from 80° to 120° C. for about 1 to about 20 hours in an organic solvent such as acetone, methanol, ethanol, n-butanol, tetrahydrofuran, benzene, toluene, diethylformamide, dimethylsulfoxide or a mixture thereof. It is preferred to conduct the reaction while removing water formed as a by-product during the reaction out of the reaction system, whereby in many cases the reaction proceeds smoothly. Further, in many cases, the reaction proceeds smoothly by the addition of an acid such as p-toluenesulfonic acid. Accordingly, the addition of such an acid is preferred. The β-mercaptoethylamine represented by the general formula III may be used in the form of its hydrochloride. In such a case, a base such as triethylamine, pyridine or potassium carbonate may be added for neutralization to let it react as a free base.

Among the compounds represented by the general formula I', a compound where $R^2$ is a lower alkylcarbamoyl group or a lower alkenylcarbamoyl group may also be obtained by reacting a compound of the general formula I' where $R^2$ is a lower alkoxycarbonyl group with a lower alkyl amine or a lower alkenyl amine, respectively, in accordance with a conventional method.

Further, when a compound of the general formula I' is reacted with a lower alkylhalide, a compound of the general formula I where $R^3$ is a lower alkyl group is obtainable; when it is reacted with a lower acyl halide or a lower alkanoic acid anhydride, a compound having a lower acyl group as $R^3$ is obtainable; when it is reacted with a lower alkyl isocyanate, a compound having a lower alkylcarbamoyl group as $R^3$ is obtainable; when it is reacted with a lower alkylisothiocyanate, a compound having a lower alkylthiocarbamoyl group as $R^3$ is obtainable; and when it is reacted with a phenylisocyanate, a compound having a phenylcarbamoyl group as $R^3$ is obtainable.

An acid addition salt of the compound presented by the general formula I may be prepared, for instance, by mixing the compound of the formula I with the above-mentioned inorganic or organic acid in a solvent such as methanol, ethanol or an ether in accordance with a conventional method.

The starting material represented by the general formula II may be prepared in accordance with a conventional method as represented by the following reaction formula.

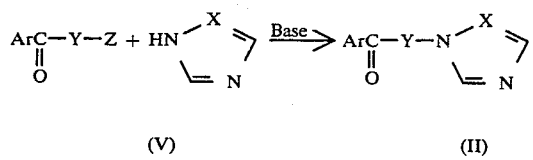

(V)    (II)

where X, Y and Ar are as defined above with respect to the general formula I, and Z is a halogen atom. The aryl haloalkyl ketone represented by the general formula V used as the starting material in this reaction may be prepared in accordance with a conventional method, for instance, by halogenation of an aryl alkyl ketone or by a Friedel-Crafts reaction of ArH with

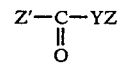

where Z' is a halogen atom.

Another starting material i.e. a β-mercaptomethylamine represented by the general formula III may be prepared, for instance, by a method disclosed in J. Org. Chem., 28, 1236 (1963), or J. Med. Chem., 8, 762 (1965).

The thiazolidine compound of the present invention has at least one asymmetric carbon atom, and various isomers exist. The compound of the present invention is usually obtained as a mixture of its isomers and as such exhibit fungicidal activities. However, if necessary, the isomers may be separated from one another. For the separation, conventional methods for the separation of isomers may be employed.

The thiazolidine derivatives of the present invention thus obtained are all novel compounds. The compounds of the present invention have strong fungicidal effectiveness against a wider range of plant diseases such as rice blast, rice sheath blight, gray mold of various crop plants, sclerotinia rot, rusts of wheats and powdery mildew of various crop plants, as compared with the conventional imidazole type or triazole type fungicides. Benzimidazole type fungicides such as benomyl or thiophenate-methyl and 3,5-dichloroaniline type fungicides such as iprodine, procymidone or vinclozolin which are presently used for the prevention of e.g. gray mold, have practical problems such that the respective resistant fungi do appear. The thiazolidine derivatives of the present invention exhibit extremely high fungicidal activity also against these resistant fungi.

Further, the thiazolidine derivatives of the present invention have good penetrability into plants and yet exhibit no substantial phytotoxicity against the plants. They also show little toxicity against human, animals or fish. Thus, they are extremely useful for the prevention of plant diseases.

When the thiazolidine derivatives of the present invention are used as an agricultural and horticultural fungicide, they may be used by themselves, but in order to facilitate the distribution of the active ingredient in the practical application, it is preferred to use them in the form of an emulsion, wettable powder or dust by adding a carrier or an adjuvant such as a surfactant in accordance with a conventional method.

As a liquid carrier (i.e. a solvent) to be used for the agricultural or horticultural fungicide of the present invention, there may be used, for instance, water, an alcohol such as methyl alcohol, ethyl alcohol or ethylene glycol, a ketone such as acetone, methylethyl ketone or cyclohexanone, an ether such as ethylether, dioxane or cellosolve, an aliphatic hydrocarbon such as kerosine or fuel oil, an aromatic hydrocarbon such as benzene, toluene, xylene, solvent naphtha or methyl naphthalene, a halogenated hydrocarbon such as dichloroethane, trichlorobenzene or carbon tetrachloride, an acid amide such as dimethyl formamide, an ester such as ethylacetate, butylacetate or a glycerin ester of a fatty acid, or a nitrile such as acetonitrile. These carriers may be used alone or in combination as a mixture of two or more.

As a solid carrier (i.e. a filler), there may be used clays such as kaolin or bentonite, talcs such as talc or pyrophylite, mineral powders such as diatomaseous earth or an oxide such as white carbon, or vegetable powders such as soybean powder or carboxymethylcellulose. These carriers may be used alone or in combination as a mixture of two or more.

Further, a surfactant may be used as a spreader, a disperser, an emulsifier or a penetrant. As such a surfactant, there may be mentioned a non-ionic surfactant such as polyoxyethyl alkylallylether or polyoxyethylene sorbitolmonolaurate, a cationic surfactant such as alkyl dimethylbenzyl ammonium chloride or alkyl pyridinium chloride, an anionic surfactant such as alkyl benzene sulfonate, lignine sulfonate higher alcohol sulfate, or an amphoteric surfactant such as alkyldimethylbataine or dodecyl aminoethyl glycine. These surfactants may be used alone or in combination as a mixture of two or more, depending upon the particular application.

The proportions of the compound of the present invention as an active ingredient, the carrier and the surfactant are for instance as follows.

|   | Compound of the present invention | Carrier | Surfactant |
| --- | --- | --- | --- |
| Emulsion | 10–50 part by weight | 10–80 part by weight | 3–20 part by weight |
| Wettable powder | 5–80 part by weight | 10–90 part by weight | 1–20 part by weight |
| Dust | 1–5 part by weight | 95–99 part by weight |  |

When using the emulsion or the wettable powder, it is further diluted with e.g. water before being applied. The amount of the application may vary depending upon the plant disease to be treated. However, it is usual that a solution or dispersion containing from 10 to 5000 ppm of the compound of the present invention as the effective ingredient is applied in an amount of 10 to 500 1/10 are.

Further, the fungicidal composition of the present invention may be used in combination with other active ingredients such as other fungicides, insecticides or acaricides so long as such additional active ingredients do not adversely affect the fungicidal activities of the active ingredient of the present invention.

Now, the present invention will be described in further detail with reference to Working Examples for the production of the compounds of the present invention, Preparation Examples for the preparation of fungicidal compositions and Test Examples for the prevention of plant diseases by the fungicides of the present invention. It should be understood, however, that the present invention is by no means restricted to these specific Examples. In the Examples, "parts" means "parts by weight".

The structures of all the compounds of the present invention prepared by the Working Examples were confirmed by their elemental analysis, IR spectra and NMR spectra.

WORKING EXAMPLE 1

25.6 g of 2,4-dichloro-ω-(1H-1,2,4-triazole-1-yl)-acetophenone, 22.7 g of β-mercaptoethylamine hydrochloride and 20.2 g of triethylamine were added to a solvent mixture comprising 200 ml of toluene and 200 ml of n-butanol, and the mixture was reacted for 4 hours under reflux. During this reaction, water formed as a by-product was removed by means of a water separator. After the reaction, the reaction mixture was cooled and washed with water, and then the solvent was distilled off under reduced pressure. The residue was recrystallized from a solvent mixture of ethyl acetate and n-hexane, whereby 21.7 g of 2-(2,4-dichlorophenyl)-2-(1H-1,2,4-triazole-1-yl-methyl)-thiazolidine (Compound No. 6 in Table 1) was obtained.

In a similar manner, Compound Nos. 1, 2, 4, 5, 9, 10, 23, 24, 29, 30, 31, 32 and 33 listed in Table 1 were obtained.

WORKING EXAMPLE 2

The reaction was conducted in the same manner as in Working Example 1 except that 20.1 g of 4-methyl-ω-(1H-1,2,4-triazole-1-yl)-acetophenone was used instead of 2,4-dichloro-ω-(1H-1,2,4-triazole-1-yl)-acetophenone. The residue was purified by silica gel column chromatography using a solvent mixture of chloroform and ethyl acetate as the developer, whereby 17.5 g of 2-(4-methylphenyl)-2-(1H-1,2,4-triazole-1-yl methyl)-thiazolidine (Compound No. 12 in Table 1) was obtained.

In a similar manner, Compound Nos. 3, 7, 8, 11, 13, 14, 15, 16, 18, 22, 15, 18, 40, 41, 45 and 55 listed in Table 1 were obtained.

WORKING EXAMPLE 3

19.0 g of 2,4-dichloro-ω-bromopropiophenone obtained by the Friedel-Crafts reaction of m-dichlorobenzene with β-bromopropionic acid chloride, 5.1 g of 1H-1,2,4-triazole and 7.5 g of triethylamine were added to 200 ml of ethanol, and the mixture was reacted overnight at room temperature. After the reaction, ethanol was distilled off under reduced pressure, and after an addition of water, the mixture was extracted with ethyl acetate. The extracted product was purified by silica gel chromatography using ethyl acetate as the developer, whereby 12.0 g of 2,4-dichloro-ω-(1H-1,2,4-triazole-1-yl)-propiophenone was obtained. The melting point was from 33° to 34° C.

6.0 g of 2,4-dichloro-ω-(1H-1,2,4-triazole-1-yl)-propiophenone thus obtained, 5.8 g of β-mercaptoethylamine hydrochloride and 5.2 g of triethylamine were added to a solvent mixture comprising 50 ml of toluene and 200 ml of n-butanol, and the mixture was reacted for 4 hours under reflux. During the reaction, water formed as a by-product was removed by means of a water separator. After the reaction, the reaction mixture was cooled and washed with water, and the solvent was distilled off under reduced pressure. The residue was purified by silica gel column chromatography using ethyl acetate as the developer, whereby 1.4 g of 2-(2,4-dichlorophenyl)-2-(1H-1,2,4-triazole-1-yl ethyl)-thiazolidine (Compound No. 19 in Table 1) was obtained.

WORKING EXAMPLE 4

3.83 g of 2,4-dichloro-ω-(1H-1,2,4-triazole-1-yl)-acetophenone, 4.24 g of β-mercapto-β-ethyl-ethylamine hydrochloride and 3.04 g of triethylamine were added to a solvent mixture comprising 50 ml of toluene and 50 ml of n-butanol, and the mixture was reacted for 8 hours under reflux. During the reaction, water formed as a by-product was removed by means of a water separator. After the reaction, reaction mixture was cooled and washed with water, and the solvent was distilled off under reduced pressure. The residue was purified by silica gel column chromatography using a solvent mixture of chloroform and ethyl acetate as the developer, whereby 2-(2,4-dichlorophenyl)-2-(1H-1,2,4-triazole-1-yl methyl)-5-ethyl triazolidine was separated into two groups of diastereomers (Compound Nos. 34 and 35 in Table 1).

In a similar manner, Compound Nos. 26, 27, 36, 37, 38 and 39 listed in Table 1 were obtained.

WORKING EXAMPLE 5

3.84 g of 2,4-dichloro-ω-(1H-1,2,4-triazole-1-yl)-acetophenone, 3.83 g of β-mercapto-α-methyl-ethylamine hydrochloride, 0.29 g of p-toluene sulfonic acid monohydrate and 3.04 g of triethylamine were added to a solvent mixture comprising 50 ml of toluene and 50 ml of n-butanol, and the mixture was reacted for 8 hours under reflux. During the reaction, water formed as a by-product was removed by means of a water separator. After the reaction, the reaction mixture was cooled and washed with water, and the solvent was distilled off under reduced pressure. The residue was purified by silica gel column chromatography using a solvent mixture of chloroform and ethyl acetate as the developer, whereby 2-(2,4-dichlorophenyl)-2-(1H-1,2,4-triazole-1-yl methyl)-4-methyl thiazolidine was separated into two groups of diastereomers (Compound Nos. 42 and 43 in Table 1). In a similar manner, Compound No. 44 listed in Table 1 was obtained.

WORKING EXAMPLE 6

1.87 g of 2-(2,4-dichlorophenyl)-2-(1H-1,2,4-triazole-1-yl methyl)-4-methoxycarbonyl thiazolidine (Compound No. 24) prepared in the same manner as in Working Example 2 and 3.0 g of n-propylamine were dissolved in 20 ml of methanol and reacted at a temperature of 60° C. for 1 hour. After distilling off methanol under reduced pressure, the reaction product was purified by silica gel column chromatography using a solvent mixture of chloroform and ethyl acetate as the developer, whereby 0.8 g of 2-(2,4-dichlorophenyl)-2-(1H-1,2,4-triazole-1-yl methyl)-4-(n-propylaminocarbonyl)thiazolidine (Compound No. 46 in Table 1) was obtained.

In a similar manner, Compound No. 47 listed in Table 1 was obtained.

WORKING EXAMPLE 7

1.58 g of 2-(2,4-dichlorophenyl)-2-(1H-1,2,4-triazole-1-yl methyl)-thiazolidine prepared in the same manner as in Working Example 1 except that β-mercaptoethylamine hydrochloride was used instead of β-mercapto-β-methyl-ethylamine hydrochloride, was mixed with 2.0 g of acetic anhydride, and the mixture was reacted at 120° C. for 4 hours. After the reaction, the reaction product was purified by silica gel column chromatography using a solvent mixture of chloroform and methanol as the developer, whereby 0.6 g of 2-(2,4-dichlorophenyl)-2-(1H-1,2,4-triazole-1-yl methyl)-3-acetyl thiazolidine (Compound No. 48 in Table 1) was obtained.

Compound Nos. 49, 50, 51 and 52 listed in Table 1 were prepared in a manner similar to above except that instead of acetic anhydride, the corresponding isocyanate or isothiocyanate was used.

WORKING EXAMPLE 8

1.58 g of 2-(2,4-dichlorophenyl)-2-(1H-1,2,4-triazole-1-yl methyl)-thiazolidine (Compound No. 6) prepared in Working Example 1, was dissolved in 20 ml of ethyl acetate, and hydrogen chloride gas was blown into the solution. The precipitated crystals were collected by filtration, whereby 1.7 g of 2-(2,4-dichlorophenyl)-2-(1H-1,2,4-triazole-1-yl methyl)-thiazolidine hydrochloride (Compound No. 20) was obtained. The melting point was from 141.0° to 143° C. (decomposed).

In a similar manner, 2-(1H-1,2,4-triazole-1-yl methyl)-5-methyl thiazolidine hydrochloride (Compound No. 53) was obtained. The melting point was from 116.0 to 117.0 (decomposed).

WORKING EXAMPLE 9

1.58 g of 2-(2,4-dichlorophenyl)-2-(1H-1,2,4-triazole-1-yl methyl)-thiazolidine (Compound No. 6) prepared in Working Example 1, was dissolved in 20 ml of ethyl acetate, and 0.7 g of concentrated nitric acid was added thereto. After adding 50 ml of ether, the precipitated crystals were collected by filtration, whereby 1.8 g of 2-(2,4-dichlorophenyl)-2-(1H-1,2,4-triazole-1-yl methyl)-thiazolidine nitrate (Compound No. 21) was obtained. The melting point was from 141.5° to 142.5° C. (decomposed).

WORKING EXAMPLE 10

1.0 g of 2-(2,4-dichlorophenyl)-2-(1H-1,2,4-triazole-1-yl methyl)-5-methyl thiazolidine (Compound No. 32) prepared in the same manner as in Working Example 1, was dissolved in 20 ml of methanol, and 2.0 g of oxalic acid dihydrate was added and dissolved therein under heating. After cooling the reaction mixture, 50 ml of water was added and then precipitated crystals were collected by filtration, whereby 0.9 g of 2-(2,4-dichlorophenyl)-2-(1H-1,2,4-triazole-1-yl methyl)-5-methyl thiazolidine oxalate (Compound No. 54) was obtained. The melting point was from 133.0° to 134.0° C.

WORKING EXAMPLE 11

2.0 g of 2-(2,4-dichlorophenyl)-2-(1H-1,2,4-triazole-1-yl methyl) thiazolidine used in Working Example 7 was dissolved in anhydrous tetrahydrofuran. After cooling the solution to −50° C., 4.5 ml of a n-hexane solution containing 15% of n-butyl lithium was added and the mixture was stirred for 30 minutes at the same temperature. Then, 2.2 g of ethyl iodide was added and the mixture was reacted for 1 hour at the same temperature. Then, the temperature was gradually raised to room temperature. After distilling off tetrahydrofuran under reduced pressure, the reaction product was purified by silica gel column chromatography using a solvent mixture of chloroform and ethyl acetate as the developer, whereby 1.0 g of 2-(2,4-dichlorophenyl)-2-(1H-1,2,4-triazole-1-yl methyl)-3-ethyl thiazolidine (Compound No. 56 in Table 1) was obtained.

In a similar manner, Compound No. 57 listed in Table 1 was obtained.

The Compounds prepared in the foregoing Working Examples are shown in Table 1.

TABLE 1

| Compound No. | Ar | Y | X | R¹ | R² | R³ | isomers[*1] | melting point or refractive index |
|---|---|---|---|---|---|---|---|---|
| 1 | phenyl | CH$_2$ | N | H | H | H | racemic modification | m.p. 91.0–91.5° C. |
| 2 | phenyl | CH$_2$ | CH | H | H | H | racemic modification | m.p. 100.5–101.0° C. |
| 3 | 2-Cl-phenyl | CH$_2$ | N | H | H | H | racemic modification | m.p. 91.0–92.0° C. |
| 4 | 4-Cl-phenyl | CH$_2$ | N | H | H | H | racemic modification | m.p. 119.0–119.5° C. |
| 5 | 4-Cl-phenyl | CH$_2$ | CH | H | H | H | racemic modification | m.p. 160.0–160.5° C. |
| 6 | 2,4-Cl$_2$-phenyl | CH$_2$ | N | H | H | H | racemic modification | m.p. 124.5–125.0° C. |
| 7 | 2,4-Cl$_2$-phenyl | CH$_2$ | CH | H | H | H | racemic modification | m.p. 141.0–142.0° C. |
| 8 | 2,4-Cl$_2$-phenyl | CH$_2$ | N | H | H | H | racemic modification | n$_D^{25}$ 1.608 |
| 9 | 4-Br-phenyl | CH$_2$ | N | H | H | H | racemic modification | m.p. 132.0–133.0° C. |
| 10 | 4-F-phenyl | CH$_2$ | N | H | H | H | racemic modification | m.p. 100.0–100.5° C. |
| 11 | 3-CH$_3$-phenyl | CH$_2$ | N | H | H | H | racemic modification | m.p. 99.0–100.0° C. |
| 12 | 4-CH$_3$-phenyl | CH$_2$ | N | H | H | H | racemic modification | m.p. 104.5–105.0° C. |
| 13 | 2,4-(CH$_3$)$_2$-phenyl | CH$_2$ | N | H | H | H | racemic modification | m.p. 128.0–129.0° C. |
| 14 | 3-CH$_3$O-phenyl | CH$_2$ | N | H | H | H | racemic modification | n$_D^{25}$ 1.602 |
| 15 | 4-CH$_3$O-phenyl | CH$_2$ | N | H | H | H | racemic modification | m.p. 86.0–87.0° C. |

TABLE 1-continued

Structure:

$$\begin{array}{c} R^1 \\ \phantom{x} \end{array} \begin{array}{c} S \\ \phantom{x} \end{array} \begin{array}{c} Ar \\ \phantom{x} \end{array}$$

with ring containing R¹, R², N–R³, S, and C(Ar)(Y–N(X)–...) where the N-X group forms a triazole/imidazole ring.

| Compound No. | Ar | Y | X | R¹ | R² | R³ | isomers*¹ | melting point or refractive index |
|---|---|---|---|---|---|---|---|---|
| 16 | 4-biphenylyl | CH₂ | N | H | H | H | racemic modification | amorphous solid |
| 17 | 2-thienyl | CH₂ | N | H | H | H | racemic modification | m.p. 79.0–79.5° C. |
| 18 | 2-naphthyl | CH₂ | N | H | H | H | racemic modification | m.p. 122.0–122.5° C. |
| 19 | 2,4-dichlorophenyl | CH₂CH₂ | N | H | H | H | racemic modification | m.p. 135.0–136.0° C. |
| 20*² | 2,4-dichlorophenyl | CH₂ | N | H | H | H | racemic modification | m.p. 141.0–143.0° C. (decomposed) |
| 21*³ | 2,4-dichlorophenyl | CH₂ | N | H | H | H | racemic modification | m.p. 141.5–142.5° C. (decomposed) |
| 22 | phenyl | CH₂ | N | CH₃ | H | H | M | $n_D^{25}$ 1.587 |
| 23 | 4-methylphenyl | CH₂ | N | CH₃ | H | H | M | m.p. 85–89° C. |
| 24 | 4-chlorophenyl | CH₂ | N | CH₃ | H | H | M | m.p. 89–93° C. |
| 25 | 3-methoxyphenyl | CH₂ | N | CH₃ | H | H | M | $n_D^{25}$ 1.577 |
| 26 | 4-chlorophenyl | CH₂ | N | H | —CO₂C₂H₅ | H | A | $n_D^{25}$ 1.564 |
| 27 | 4-chlorophenyl | CH₂ | N | H | —CO₂C₂H₅ | H | B | $n_D^{25}$ 1.574 |
| 28 | 2-chlorophenyl | CH₂ | N | H | —CO₂CH₃ | H | M | $n_D^{25}$ 1.580 |
| 29 | 4-fluorophenyl | CH₂ | N | CH₃ | H | H | M | m.p. 108–110° C. |
| 30 | 4-biphenylyl | CH₂ | N | C₂H₅ | H | H | M | m.p. 90–6° C. |
| 31 | 2,4-dichlorophenyl | CH₂ | CH₂ | CH₃ | H | H | M | m.p. 148–9° C. |

TABLE 1-continued

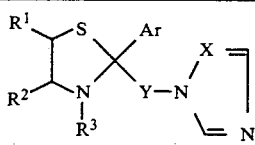

| Compound No. | Ar | Y | X | R¹ | R² | R³ | isomers*1 | melting point or refractive index |
|---|---|---|---|---|---|---|---|---|
| 32 | 2,4-Cl₂C₆H₃ | CH₂ | N | CH₃ | H | H | M | m.p. 118–124° C. |
| 33 | 2,4-Cl₂C₆H₃ | —CH(CH₃)— | N | CH₃ | H | H | M | m.p. 133–135° C. |
| 34 | 2,4-Cl₂C₆H₃ | CH₂ | N | C₂H₅ | H | H | A | $n_D^{25}$ 1.582 |
| 35 | 2,4-Cl₂C₆H₃ | CH₂ | N | C₂H₅ | H | H | B | m.p. 128–129° C. |
| 36 | 2,4-Cl₂C₆H₃ | CH₂ | N | C₃H₇(n) | H | H | A | m.p. 75–76° C. |
| 37 | 2,4-Cl₂C₆H₃ | CH₂ | N | C₃H₇(n) | H | H | B | viscous liquid |
| 38 | 2,4-Cl₂C₆H₃ | CH₂ | N | C₄H₉(i) | H | H | A | $n_D^{25}$ 1.572 |
| 39 | 2,4-Cl₂C₆H₃ | CH₂ | N | C₄H₉(i) | H | H | B | $n_D^{25}$ 1.555 |
| 40 | 2,4-Cl₂C₆H₃ | CH₂ | N | C₆H₁₃(n) | H | H | M | $n_D^{25}$ 1.577 |
| 41 | 2,4-Cl₂C₆H₃ | CH₂ | N | C₆H₅ | H | H | M | viscous liquid |
| 42 | 2,4-Cl₂C₆H₃ | CH₂ | N | H | CH₃ | H | A | $n_D^{25}$ 1.579 |
| 43 | 2,4-Cl₂C₆H₃ | CH₂ | N | H | CH₃ | H | B | $n_D^{25}$ 1.591 |
| 44 | 2,4-Cl₂C₆H₃ | CH₂ | N | H | C₂H₅ | H | M | $n_D^{25}$ 1.581 |

TABLE 1-continued

[structure formula shown at top]

| Compound No. | Ar | Y | X | R¹ | R² | R³ | isomers*1 | melting point or refractive index |
|---|---|---|---|---|---|---|---|---|
| 45 | 2,4-Cl₂-C₆H₃ | CH₂ | N | H | —CO₂CH₃ | H | M | amorphous solid |
| 46 | 2,4-Cl₂-C₆H₃ | CH₂ | N | H | —CONHC₃H₇(n) | H | M | amorphous solid |
| 47 | 2,4-Cl₂-C₆H₃ | CH₂ | N | H | —CONHCH₂CH=CH₂ | H | M | amorphous solid |
| 48 | 2,4-Cl₂-C₆H₃ | CH₂ | N | H | H | COCH₃ | racemic modification | $n_D^{25}$ 1.591 |
| 49 | 2,4-Cl₂-C₆H₃ | CH₂ | N | CH₃ | H | COCH₃ | M | $n_D^{25}$ 1.571 |
| 50 | 2,4-Cl₂-C₆H₃ | CH₂ | N | H | H | —CONHCH₃ | racemic modification | $n_D^{25}$ 1.589 |
| 51 | 2,4-Cl₂-C₆H₃ | CH₂ | N | H | H | —CSNHCH₃ | racemic modification | $n_D^{25}$ 1.621 |
| 52 | 2,4-Cl₂-C₆H₃ | CH₂ | N | H | H | —CONH—C₆H₅ | racemic modification | amorphous solid |
| 53*4 | 2,4-Cl₂-C₆H₃ | CH₂ | N | CH₃ | H | H | M | m.p. 116.0–117.0° C. (decomposed) |
| 54*5 | 2,4-Cl₂-C₆H₃ | CH₂ | N | CH₃ | H | H | M | m.p. 133.0–134.0° C. |
| 55 | 2,4-Cl₂-C₆H₃ | CH₂ | N | CH₃ | CH₃ | H | M | viscous liquid |
| 56 | 2,4-Cl₂-C₆H₃ | CH₂ | N | H | H | C₂H₅ | racemic modification | $n_D^{25}$ 1.592 |

TABLE 1-continued

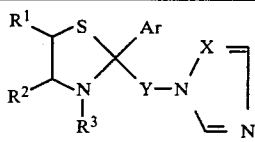

| Compound No. | Ar | Y | X | R¹ | R² | R³ | isomers[*1] | melting point or refractive index |
|---|---|---|---|---|---|---|---|---|
| 57 | ![2,4-dichlorophenyl] | CH₂ | N | H | H | C₃H₇(i) | racemic modification | $n_D^{25}$ 1.584 |

[*1] M represents a mixture of diastereomers, and A and B represent two groups of diastereomers separated from each other.
[*2] Hydrochloride
[*3] Nitrate
[*4] Hydrochloride
[*5] Oxalate

PREPARATION EXAMPLE 1

Wettable powder

50 Parts of Compound No. 4, 45 parts of talc and 5 parts of Sorpol 8070 (trade mark, a surfactant comprising a sulfuric acid ester of a higher alcohol as the major component) were uniformly pulverized and mixed to obtain wettable powder.

PREPARATION EXAMPLE 2

Wettable powder

40 Parts of Compound No. 44, 10 parts of white carbon, 47 parts of diatomaceous earth and 3 parts of Sorpol 5039 (trade mark, a surfactant comprising a polyoxyethylene alkylaryl ester sulfonate as the major component) were uniformly pulverized and mixed to obtain wettable powder.

PREPARATION EXAMPLE 3

Emulsion

30 Parts of Compound No. 6, 15 parts of Sorpol 3005X (trade mark, a mixture of a non-ionic surfactant and an anionic surfactant), 25 parts of xylene and 30 parts of dimethylformamide were mixed and dissolved to obtain an emulsion.

PREPARATION EXAMPLE 4

Dust

2 Parts of Compound No. 35 and 98 parts of N,N-kaolin clay (manufactured by Tsuchiya Kaolin Company) were mixed and pulverized to obtain a dust.

TEST EXAMPLE 1

Fungicidal activity against rice blast

A fungicide formulation was applied to a rice plant (cultivar: Akinishiki) or 3rd-4th leaf stage cultured in a pot having a diameter of 6 m. The fungicide formulation was the one prepared by diluting a wettable powder obtained by pulverizing and mixing 20 parts of a compound of the present invention, 5 parts of an alkyl benzene sulfonic acid type wetting agent and 75 parts of diatomaceous earth, with water to a predetermined concentration. The fungicide formulation was applied to the foliage at a rate of 10 ml per pot. After drying in air the applied solution, spores of *Pyricularia oryzae* cultured in an oatmeal culture medium were sprayed for inoculation. The inoculated rice plant was kept in a moist chamber at 27° C. for 24 hours and then left in a green house for 3 days. The number of disease stigmata appeared on the rice plant leaves was counted, and the protective value was calculated by the following formula:

Protective value (%) =

$$\frac{\text{(Number of disease stigmata per leaf untreated)} - \text{(Number of disease stigmata per lead treated)}}{\text{(Number of disease stigmata per leaf untreated)}} \times 100$$

The results obtained are shown in Table 2.

TABLE 2

Test results on fungicidal activity against rice blast

| Compound No. | Concentration of active ingredient | Protective value (%) |
|---|---|---|
| 6 | 500 ppm | 97 |
| 8 | 500 ppm | 91 |
| 16 | 500 ppm | 89 |
| 21 | 500 ppm | 98 |
| 22 | 500 ppm | 97 |
| Comparative* fungicide triadimefon | 500 ppm | 35 |

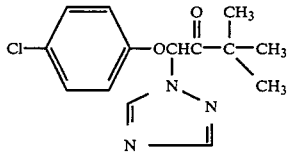

TEST EXAMPLE 2

Tests on the fungicidal activities of the Compounds listed in Table 3 were conducted in the same manner as in Test Example 1. The results thereby obtained are shown in Table 3.

TABLE 3

Test results on fungicidal activity against rice blast

| Compound No. | Concentration of active ingredient | Protective value (%) |
|---|---|---|
| 24 | 500 ppm | 92 |
| 29 | 500 ppm | 91 |
| 30 | 500 ppm | 95 |
| 31 | 500 ppm | 99 |
| 33 | 500 ppm | 98 |
| 34 | 500 ppm | 95 |

TABLE 3-continued

Test results on fungicidal activity against rice blast

| Compound No. | Concentration of active ingredient | Protective value (%) |
|---|---|---|
| 35 | 500 ppm | 94 |
| 38 | 500 ppm | 98 |
| 39 | 500 ppm | 97 |
| 40 | 500 ppm | 98 |
| 42 | 500 ppm | 96 |
| 44 | 500 ppm | 95 |
| 55 | 500 ppm | 100 |
| 56 | 500 ppm | 99 |
| 57 | 500 ppm | 92 |
| Comparative fungicide triadimefon | 500 ppm | 35 |

TEST EXAMPLE 3

Fungicidal activity against rice sheath blight

A wettable powder prepared in the same manner as in Test Example 1 was diluted with water to a predetermined concentration and applied at a rate of 10 ml per pot to the foliage of a rice plant (cultivar: Nakateshinsenbon) of 3rd–4th leaf stage cultivated in a pot having a diameter of 6 cm. After drying in air the applied solution, a dispersion of mycelia of Rhizoctonia solani cultivated in a yeast-glucose culture medium was sprayed for inoculation. The inoculated rice plant was kept in a moist chamber at 29° C. for 24 hours and then left in a green house for 3 days. The diseased area on the rice plant leaves was measured and the disease index was calculated in the manner as indicated in Test Example 5. Then, the fungicidal value was calculated by the following formula:

$$\text{Protective value (\%)} = \frac{\text{(Disease index per leaf untreated)} - \text{(Disease index per leaf treated)}}{\text{(Disease index per leaf untreated)}} \times 100$$

TABLE 4

Test results on the fungicidal activity against rice sheath blight

| Compound No. | Concentration of active ingredient | Protective value (%) |
|---|---|---|
| 1 | 500 ppm | 88 |
| 2 | 500 ppm | 99 |
| 3 | 500 ppm | 96 |
| 4 | 500 ppm | 99 |
| 5 | 500 ppm | 93 |
| 7 | 500 ppm | 94 |
| 9 | 500 ppm | 94 |
| 10 | 500 ppm | 97 |
| 12 | 500 ppm | 83 |
| 13 | 500 ppm | 94 |
| 17 | 500 ppm | 95 |
| 20 | 500 ppm | 100 |
| 21 | 500 ppm | 100 |

TEST EXAMPLE 4

Test on the fungicidal activities of the Compounds listed in Table 5 were conducted in the same manner as in Test Example 3. The results thereby obtained are shown in Table 5.

TABLE 5

Test results on the fungicidal activity against rice sheath blight

| Compound No. | Concentration of active ingredient | Protective value (%) |
|---|---|---|
| 22 | 500 ppm | 90 |
| 24 | 500 ppm | 91 |
| 25 | 500 ppm | 100 |
| 29 | 500 ppm | 98 |
| 31 | 500 ppm | 100 |
| 32 | 500 ppm | 100 |
| 33 | 500 ppm | 98 |
| 34 | 500 ppm | 100 |
| 35 | 500 ppm | 100 |
| 38 | 500 ppm | 90 |
| 39 | 500 ppm | 93 |
| 40 | 500 ppm | 97 |
| 42 | 500 ppm | 99 |
| 43 | 500 ppm | 99 |
| 44 | 500 ppm | 87 |
| 48 | 500 ppm | 95 |
| 50 | 500 ppm | 96 |
| 51 | 500 ppm | 98 |
| 53 | 500 ppm | 100 |
| 56 | 500 ppm | 94 |

TEST EXAMPLE 5

Fungicidal activity against cucumber gray mold

A wettable powder prepared in the same manner as in Test Example 1 was diluted with water to a predetermined concentration and applied at a rate of 10 ml per pot to the foliage of a cucumber plant (cultivar: Chikanarisuyou) of cotyledonal stage cultivated in a pot having a diameter of 6 cm. After drying in air the applied solution, Botrytis cinerea cultured in a yeast-glucose liquid culture medium by a shaking culture method was sprayed for inoculation. After the inoculation, the cucumber plant was kept in a moist room at 23° C. for 4 days and then the diseased area was measured. Based on the results of the examination, the protective value was calculated in accordance with the following formula. The results thereby obtained are shown in Table 6.

Diseased rate

The diseased area ratio of each leaf was measured and evaluated in accordance with indexes of 0, 1, 3 and 5 depending upon the diseased degree. The number $n_0$, $n_1$, $n_3$ or $n_5$ of leaves corresponding to each disease index was counted, and the diseased rate was calculated in accordance with the following formula. (n represents a total number of examined leaves.)

| Disease index | Diseased area ratio |
|---|---|
| 0 | No disease |
| 1 | up to ¼ of the leaf area diseased |
| 3 | ¼–½ of the leaf diseased |
| 5 | more than ½ of the leaf diseased |

$$\text{Diseased rate} = \frac{0 \times n_0 + 1 \times n_1 + 3 \times n_3 + 5 \times n_5}{n}$$

Protective value $$\text{Protective value (\%)} = \frac{\text{(Diseased rate untreated)} - \text{(Diseased rate treated)}}{\text{(Diseased rate untreated)}} \times 100$$

TABLE 6

Test results on the fungicidal activity against cucumber gray mold

| Compound No. | Protective value (%) Concentration of active ingredient | |
|---|---|---|
| | 500 ppm | 200 ppm |
| 1 | 90 | 81 |
| 3 | 95 | 90 |
| 4 | 100 | 100 |
| 6 | 100 | 100 |
| 7 | 100 | 94 |
| 9 | 100 | 92 |
| 10 | 98 | 85 |
| 16 | 100 | 98 |
| 20 | 100 | 100 |
| 21 | 100 | 100 |
| Comparative* fungicide etaconazole | 96 | 55 |

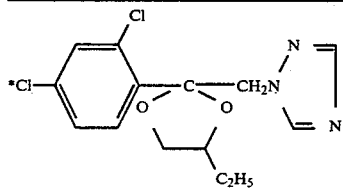

TEST EXAMPLE 6

Test on the fungicidal activities of the compounds listed in Table 7 were conducted in the same manner as in Test Example 5. The results thereby obtained are shown in Table 7.

TABLE 7

Test results on the fungicidal activity against cucumber gray mold

| Compound No. | Protective value (%) Concentration of active ingredient | |
|---|---|---|
| | 500 ppm | 200 ppm |
| 23 | 97 | 83 |
| 24 | 100 | 99 |
| 29 | 98 | 88 |
| 30 | 97 | 94 |
| 31 | 97 | 96 |
| 32 | 100 | 100 |
| 34 | 100 | 100 |
| 35 | 100 | 100 |
| 39 | 100 | 98 |
| 40 | 100 | 99 |
| 42 | 95 | 92 |
| 43 | 98 | 87 |
| 44 | 99 | 96 |
| 50 | 97 | 94 |
| 51 | 100 | 95 |
| 53 | 99 | 96 |
| Comparative fungicide etaconazole | 96 | 55 |

TEST EXAMPLE 7

Fungicidal activity against cucumber powdery mildew

A wettable powder prepared in the same manner as in Test Example 1 was diluted with water to a predetermined concentration and applied at a rate of 10 ml per pot to the foliage of a cucumber plant (cultivar: Chikanarisuyou) of cotyledonal stage cultivated in a pot having a diameter of 6 cm. After drying in air the applied solution, a dispersion of spores obtained by mashing a cucumber leaf diseased with *Sphaerotheca fuliginea* was sprayed for inoculation. The inoculated plant was left in a green house for 7 to 10 days.

The diseased area ratio of each leaf was measured, and the protective value was calculated in accordance with the following formula.

$$\text{Protective value (\%)} = \frac{\text{(Average diseased area ratio untreated)} - \text{(Average diseased area ratio treated)}}{\text{(Average diseased area ratio untreated)}} \times 100$$

TABLE 8

Test results on the fungicidal activity against cucumber powdery mildew

| Compound No. | Protective value (%) Concentration of active ingredient | |
|---|---|---|
| | 500 ppm | 100 ppm |
| 1 | 100 | 87 |
| 2 | 100 | 87 |
| 3 | 100 | 100 |
| 4 | 100 | 100 |
| 5 | 100 | 95 |
| 6 | 100 | 100 |
| 7 | 100 | 100 |
| 8 | 100 | 85 |
| 9 | 100 | 100 |
| 10 | 100 | 100 |
| 11 | 100 | 88 |
| 12 | 100 | 85 |
| 13 | 100 | 83 |
| 14 | 100 | 86 |
| 15 | 100 | 93 |
| 16 | 100 | 90 |
| 17 | 97 | 85 |
| 20 | 100 | 100 |
| 21 | 100 | 100 |
| Comparative* fungicide chinomethionat | 100 | 87 |

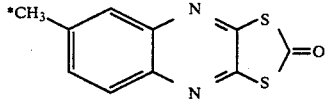

TEST EXAMPLE 8

Test on the fungicidal activities of the compounds listed in Table 9 were conducted in the same manner as in Test Example 7. The results thereby obtained are shown in Table 9.

TABLE 9

Test results on the fungicidal activity against cucumber powdery mildew

| Compound No. | Protective value (%) Concentration of active ingredient | |
|---|---|---|
| | 500 ppm | 100 ppm |
| 22 | 100 | 85 |
| 23 | 100 | 96 |
| 24 | 100 | 89 |
| 29 | 100 | 99 |
| 31 | 100 | 98 |
| 32 | 100 | 100 |
| 34 | 100 | 100 |
| 35 | 100 | 100 |
| 42 | 100 | 100 |
| 43 | 100 | 100 |
| 44 | 100 | 100 |
| 45 | 100 | 100 |
| 46 | 100 | 97 |
| 47 | 100 | 100 |
| 48 | 100 | 99 |
| 50 | 100 | 97 |
| 51 | 100 | 100 |

TABLE 9-continued

Test results on the fungicidal activity against cucumber powdery mildew

| Compound No. | Protective value (%) Concentration of active ingredient | |
|---|---|---|
| | 500 ppm | 100 ppm |
| 52 | 100 | 100 |
| 53 | 100 | 100 |
| 54 | 100 | 100 |
| 55 | 100 | 100 |
| 56 | 100 | 99 |
| 57 | 100 | 97 |
| Comparative fungicide chinomethionat | 100 | 87 |

TEST EXAMPLE 9

Systemic activity against cucumber powdery mildew

Roots of a cucumber plant (cultivar: Chikanarisuyou) of cotyledonal stage cultivated in a pot having a diameter of 6 cm was thoroughly washed with water, and then the cucumber plant was transferred to a water culture solution prepared by diluting a wettable powder obtained in the same manner as in Test Example 1, with water to a predetermined concentration. The plant was left in green house for 2 days to let the fungicide penetrate from the roots. Thereafter, a dispersion of spores obtained by mashing a cucumber leaf diseased with *Sphaerotheca fuliginea* was sprayed for inoculation, and the plant was left in the green house for 7 to 10 days.

The diseased area ratio of each leaf was measured, and the protective value was calculated in the same manner as in Test Example 7.

The results thereby obtained are shown in Table 10.

TABLE 10

Test results on the systemic activity against cucumber powdery mildew

| Compound | Concentration of active ingredient | Protective value (%) |
|---|---|---|
| 1 | 5 ppm | 100 |
| 2 | 5 | 100 |
| 3 | 5 | 100 |
| 4 | 5 | 100 |
| 5 | 5 | 100 |
| 6 | 5 | 100 |
| 7 | 5 | 100 |
| 8 | 5 | 100 |
| 9 | 5 | 100 |
| 10 | 5 | 100 |
| 11 | 5 | 100 |
| 12 | 5 | 100 |
| 13 | 5 | 88 |
| 14 | 5 | 100 |
| 15 | 5 | 80 |
| 16 | 5 | 100 |
| 17 | 5 | 100 |
| 18 | 5 | 100 |
| 19 | 5 | 100 |
| 20 | 5 | 100 |
| 21 | 5 | 100 |
| Comparative fungicide chinomethionat | 5 | 33 |

TEST EXAMPLE 10

Tests on the fungicidal activities of the compounds listed in Table 11 were conducted in the same manner as in Test Example 9. The results thereby obtained are shown in Table 11.

TABLE 11

Test results on the systemic activity against cucumber powdery mildew

| Compound No. | Concentration of active ingredient | Protective value (%) |
|---|---|---|
| 22 | 5 ppm | 100 |
| 23 | 5 | 96 |
| 24 | 5 | 100 |
| 28 | 5 | 100 |
| 29 | 5 | 100 |
| 30 | 5 | 100 |
| 31 | 5 | 100 |
| 32 | 5 | 100 |
| 33 | 5 | 100 |
| 34 | 5 | 100 |
| 35 | 5 | 100 |
| 38 | 5 | 100 |
| 39 | 5 | 100 |
| 40 | 5 | 100 |
| 42 | 5 | 100 |
| 43 | 5 | 100 |
| 44 | 5 | 100 |
| 45 | 5 | 100 |
| 46 | 5 | 100 |
| 47 | 5 | 100 |
| 48 | 5 | 100 |
| 49 | 5 | 100 |
| 50 | 5 | 100 |
| 51 | 5 | 100 |
| 52 | 5 | 100 |
| 53 | 5 | 100 |
| 54 | 5 | 100 |
| 55 | 5 ppm | 100 |
| 56 | 5 | 100 |
| 57 | 5 | 100 |
| Comparative fungicide chinomethionat | 5 | 33 |

TEST EXAMPLE 11

Fungicidal activity against wheat brown rust

A wettable powder prepared in the same manner as in Test Example 1 was diluted with water to a predetermined concentration and applied at a rate of 10 ml per pot to the foliage of a wheat (cultivar: Norin 61) of 1st-2nd leaf stage cultivated in a pot having a diameter of 6 cm. After drying in air the applied solution, a dispersion of spores obtained by mashing a wheat diseased with *Puccinia recondita* was sprayed for inoculation. The inoculated wheat was kept in moist chamber at 22° C. for 15 hours, and then left for 7 days in a green house.

The diseased area ratio of each leaf was measured, and the protective value was calculated in accordance with the following formula.

$$\text{Protective value (\%)} = \frac{\text{(Average diseased area ratio untreated)} - \text{(Average diseased area ratio treated)}}{\text{(Average diseased area ratio untreated)}} \times 100$$

The results thereby obtained are shown in Table 12.

TABLE 12

Test results on the fungicidal activity against wheat brown rust

| Compound No. | Protective value (%) Concentration of active ingredient | |
|---|---|---|
| | 500 ppm | 200 ppm |
| 1 | 100 | 96 |
| 4 | 99 | 98 |
| 5 | 100 | 96 |
| 6 | 100 | 100 |
| 7 | 100 | 92 |

TABLE 12-continued

Test results on the fungicidal activity against wheat brown rust

| | Protective value (%) Concentration of active ingredient | |
|---|---|---|
| Compound No. | 500 ppm | 200 ppm |
| 9 | 100 | 100 |
| 12 | 100 | 90 |
| 13 | 96 | 88 |
| 20 | 100 | 100 |
| 21 | 100 | 100 |
| Comparative* fungicide maneb | 99 | 95 |

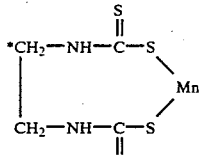

TEST EXAMPLE 12

Tests on the fungicidal activities of the compouns listed in Table 13 were conducted in the same manner as in Test Example 11.

The results thereby obtained are shown in Table 13.

TABLE 13

Test results on the fungicidal activity against wheat brown rust

| | Protective value (%) Concentration of active ingredient | |
|---|---|---|
| Compound No. | 500 ppm | 200 ppm |
| 24 | 98 | 93 |
| 30 | 97 | 98 |
| 31 | 100 | 93 |
| 32 | 100 | 100 |
| 34 | 100 | 100 |
| 35 | 100 | 100 |
| 42 | 100 | 96 |
| 43 | 100 | 90 |
| 44 | 99 | 96 |
| 53 | 100 | 100 |
| 54 | 100 | 100 |
| 55 | 100 | 95 |
| 56 | 98 | 94 |
| Comparative fungicide maneb | 99 | 95 |

TEST EXAMPLE 13

Systemic activity against wheat brown rust

Roots of a wheat (cultivar: Norin 61) of 1st-2nd leaf stage cultivated in a pot having a diameter of 6 cm were thoroughly washed with water, and then the wheat was transferred to a water culture solution prepared by diluting a wettable powder obtained in the same manner as in Test Example 1, with water to a predetermined concentration. The wheat was left in a green house for 2 days to let the fungicide penetrate from the roots. Thereafter, a dispersion of spores obtained by mashing a wheat diseased with *Puccinia recondita* was sprayed for inoculation. The inoculated wheat was kept in a moist chamber at 22° C. for 15 hours and then left for 7 days in a green house.

The protective value was calculated in the same manner as in Test Example 10. The results thereby obtained are shown in Table 14.

TABLE 14

Test results on the systemic activities against wheat brown rust

| Compound No. | Concentration of active ingredient | Protective value (%) |
|---|---|---|
| 1 | 5 ppm | 100 |
| 2 | 5 | 100 |
| 3 | 5 | 100 |
| 4 | 5 | 100 |
| 5 | 5 | 100 |
| 6 | 5 | 100 |
| 7 | 5 | 100 |
| 8 | 5 | 98 |
| 9 | 5 | 100 |
| 10 | 5 | 100 |
| 11 | 5 | 87 |
| 12 | 5 | 99 |
| 13 | 5 | 77 |
| 14 | 5 | 85 |
| 15 | 5 | 93 |
| 16 | 5 | 100 |
| 17 | 5 | 99 |
| 18 | 5 | 98 |
| 19 | 5 | 78 |
| 20 | 5 | 100 |
| 21 | 5 | 100 |
| Comparative fungicide maneb | 5 | 0 |

TEST EXAMPLE 14

Test on the systemic activities of the compounds listed in Table 15 were conducted in the same manner as in Test Example 13. The results thereby obtained are shown in Table 15.

TABLE 15

Test results on the systemic activities against wheat brown rust

| Compound No. | Concentration of active ingredient | Protective value (%) |
|---|---|---|
| 24 | 5 ppm | 100 |
| 31 | 5 | 100 |
| 32 | 5 | 100 |
| 33 | 5 | 100 |
| 34 | 5 | 100 |
| 35 | 5 | 100 |
| 38 | 5 | 100 |
| 39 | 5 | 100 |
| 40 | 5 | 100 |
| 42 | 5 | 100 |
| 43 | 5 | 100 |
| 44 | 5 | 100 |
| 48 | 5 | 100 |
| 49 | 5 | 100 |
| 50 | 5 | 100 |
| 51 | 5 | 100 |
| 53 | 5 | 100 |
| 54 | 5 | 100 |
| 55 | 5 | 98 |
| Comparative fungicide maneb | 5 | 0 |

TEST EXAMPLE 15

Fungicidal activity against lettuce sclerotinia rot

A wettable powder prepared in the same manner as in Test Example 1 was diluted with water to a predetermined concentration and applied at a rate of 20 ml per pot to a lettuce (species: great lakes 366) of 7th-9th leaf stage cultivated in a pot having a diameter of 10 cm. After drying in air the applied solution, *Sclerotinia sclerotiorum* cultivated in a yeast-glucose liquid culture medium by a shaking culture method was sprayed for inoculation. After the inoculation, the lettuce was kept in a moist chamber at 20° C. for 4 days, and then the diseased area was measured.

The diseased rate was determined in the same manner as in Test Example 5, and the protective value was calculated. The results thereby obtained are shown in Table 16.

TABLE 16

Test results on the fungicidal activity against lettuce sclerotinia rot

| Compound No. | Concentration of active ingredient | Protective value (%) |
|---|---|---|
| 3 | 500 ppm | 98 |
| 4 | 500 | 100 |
| 5 | 500 | 95 |
| 6 | 500 | 100 |
| 7 | 500 | 97 |
| 9 | 500 | 100 |
| 20 | 500 | 100 |
| 21 | 500 | 100 |

TEST EXAMPLE 16

Fungicidal activity against growth of mycelia

In a sterilized petri dish having a diameter of 80 mm, a wettable powder prepared in the same manner as in Test Example 1 was diluted with a potato dextrose agar culture medium to bring the concentration of the active ingredient to 50 ppm. A fungus infected agar piece containing one of the three types of gray mold strains identified below and cultivated in a potato dextrose agar culture medium, was inoculated to the center of the culture medium, and the inoculated culture medium was cultivated for 5 days in a constant temperature room kept at 25° C. The diameter of the grown mycelia of each strain was measured, and the growth control rate was calculated in accordance with the following formula.

Growth control rate (%) =

$$\frac{[\text{Growth of mycelia untreated (mm)}] - [\text{Growth of mycelia treated (mm)}]}{[\text{Growth of mycelia untreated (mm)}]} \times 100$$

The results thereby obtained are shown in Table 17.

TABLE 17

Test results on the fungicidal activity against the growth of mycelia

| | Strain | | |
|---|---|---|---|
| Compound No. | Botrytis*1 cinerea-1 Growth control rate (%) | Botrytis*2 cinerea-2 Growth control rate (%) | Botrytis*3 cinerea-3 Growth control rate (%) |
| 3 | 100 | 100 | 100 |
| 4 | 100 | 100 | 100 |
| 6 | 100 | 100 | 100 |
| 7 | 100 | 100 | 100 |
| 9 | 100 | 100 | 100 |
| 20 | 100 | 100 | 100 |
| 21 | 100 | 100 | 100 |
| Comparative*4 fungicide iprodione | 100 | 10 | 0 |
| Comparative*5 fungicide benomyl | 100 | 10 | 100 |

TABLE 17-continued

Test results on the fungicidal activity against the growth of mycelia

*1 Iprodione and benomyl sensitive strain
*2 Iprodione and benomyl resistant strain
*3 Iprodione resistant and benomyl sensitive strain

*4 
[Structure: CH₃\CHNHC(O)—N of iprodione with 3,5-dichlorophenyl]

*5 
[Structure: benzimidazole—NHCO₂CH₃ with CONHC₄H₉(n)]

TEST EXAMPLE 17

Tests on the fungicidal activities of the compounds listed in Table 18 were conducted in the same manner as in Test Example 16. The results thereby obtained are shown in Table 18.

TABLE 18

Test results on the fungicidal activity against the growth of mycelia

| | Strain | | |
|---|---|---|---|
| Compound No. | Botrytis *1 cineria-1 Growth control rate (%) | Botrytis *2 cineria-2 Growth control rate (%) | Botrytis *3 cinerea-3 Growth control rate (%) |
| 24 | 100 | 100 | 100 |
| 33 | 100 | 100 | 100 |
| 34 | 100 | 100 | 100 |
| 35 | 100 | 100 | 100 |
| 39 | 100 | 100 | 100 |
| 40 | 100 | 100 | 100 |
| 51 | 100 | 100 | 100 |
| Comparative fungicide iprodione | 100 | 10 | 0 |
| Comparative fungicide benomyl | 100 | 10 | 100 |

*1 Iprodione and benomyl sensitive strain
*2 Iprodione and benomyl resistant strain
*3 Iprodione resistant and benomyl sensitive strain

We claim:

1. A thiazolidine compound represented by the formula I or its acid addition salt

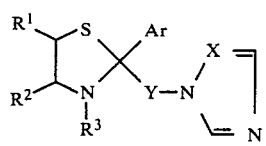

wherein
X is —CH= or —N=;
Y is —CH₂—CH₂— or

wherein R is a hydrogen atom, a methyl group, or an ethyl group;

Ar is a phenyl group which may be substituted by halogen, lower alkyl, lower alkoxy, phenyl, trifluoromethyl, a thienyl group or a naphthyl group;

$R^1$ is a hydrogen atom, a straight chain or branched chain alkyl group having from 1 to 10 carbon atoms or a phenyl group which may be unsubstituted or substituted by a lower alkyl or halogen;

$R^2$ is a hydrogen atom, a straight chain or branched chain alkyl group having from 1 to 10 carbon atoms, a phenyl group which may be unsubstituted or substituted by a lower alkyl or halogen, a lower alkoxycarbonyl group, a lower alkylcarbamoyl group or a lower alkenylcarbamoyl group; and $R^3$ is a hydrogen atom, a lower alkyl group, a lower carboxyacyl group, a lower alkylcarbamoyl group, a lower alkylthiocarbamoyl group or a phenylcarbamoyl group.

2. The compound according to claim 1 wherein Ar in the general formula I is a phenyl group having halogen at its 2-position and/or 4-position.

3. The compound according to claim 1 wherein X in the general formula I is —N═.

4. The compound according to claim 3 wherein Y in the general formula I is —CH₂—.

5. The compound according to claim 4 wherein each of $R^1$, $R^2$ and $R^3$ in the general formula I is a hydrogen atom or a straight chain or branched chain alkyl group having from 1 to 4 carbon atoms.

6. The compound according to claim 1 wherein each of $R^2$ and $R^3$ in the general formula I is a hydrogen atom.

7. A fungicidal composition comprising at least a fungicidally effective amount of a compound represented by the formula I or its acid addition salt and an agricultural carrier

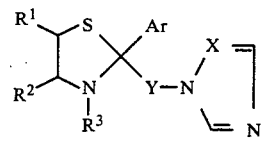 (I)

wherein
X is —CH═ or —N═;
Y is —CH₂—CH₂—or

wherein R is a hydrogen atom, a methyl group, or an ethyl group;

Ar is a phenyl group which may be substituted by halogen, lower alkyl, lower alkoxy, phenyl, trifluoromethyl, a thienyl group or a naphthyl group;

$R^1$ is a hydrogen atom, a straight chain or branched chain alkyl group having from 1 to 10 carbon atoms or a phenyl group which may be further substituted by a lower alkyl or halogen;

$R^2$ is a hydrogen atom, a straight chain or branched chain alkyl group having from 1 to 10 crbon atoms, a phenyl group which may be further substituted by a lower alkyl or halogen, a lower alkoxycarbonyl group, a lower alkylcarbamoyl group or a lower alkenylcarbamoyl group; and $R^3$ is a hydrogen atom, a lower alkyl group, a lower carboxyacyl group, a lower alkylcarbamoyl group, a lower alkylthiocarbamoyl group or a phenylcarbamoyl group.

8. The fungicidal composition according to claim 7 wherein Ar in the general formula I is a phenyl group having halogen at its 2-position and/or 4-position.

9. The fungicidal composition according to claim 7 wherein X in the general formula I is —N═.

10. The fungicidal composition according to claim 9 wherein Y in the gneral formula I is —CH₂—.

11. The fungicidal composition according to claim 10 wherein each of $R^1$, $R^2$ and $R^3$ in the general formula I is a hydrogen atom or a straight chain or branched chain alkyl group having from 1 to 4 carbon atoms.

12. The fungicidal composition according to claim 7 which comprises from 1 to 80 parts by weight of the compound of the general formula I or its acid addition salt, from 10 to 99 parts by weight of an agricultual carrier and from 0 to 20 parts by weight of other adjuvant.

* * * * *